US010258580B2

(12) United States Patent
Iuvone et al.

(10) Patent No.: US 10,258,580 B2
(45) Date of Patent: Apr. 16, 2019

(54) CANNABINOIDS FOR USE IN THE TREATMENT OF NEURODEGENERATIVE DISEASES OR DISORDERS

(75) Inventors: Teresa Iuvone, Naples (IT); Vincenzo Di Marzo, Pozzuoli (IT); Geoffrey Guy, Salisbury (GB); Stephen Wright, Salisbury (GB); Colin Stott, Salisbury (GB)

(73) Assignee: GW Pharma Limited, Cambridge (GB)

( * ) Notice: Subject to any disclaimer, the term of this patent is extended or adjusted under 35 U.S.C. 154(b) by 607 days.

(21) Appl. No.: 14/128,208

(22) PCT Filed: Jun. 29, 2012

(86) PCT No.: PCT/GB2012/051540
§ 371 (c)(1),
(2), (4) Date: Mar. 25, 2014

(87) PCT Pub. No.: WO2013/005017
PCT Pub. Date: Jan. 10, 2013

(65) Prior Publication Data
US 2014/0228438 A1    Aug. 14, 2014

(30) Foreign Application Priority Data
Jul. 1, 2011 (GB) .................................. 1111261.2

(51) Int. Cl.
*A61K 31/05* (2006.01)
*A61K 31/352* (2006.01)
*A61K 31/192* (2006.01)

(52) U.S. Cl.
CPC ............ *A61K 31/05* (2013.01); *A61K 31/192* (2013.01); *A61K 31/352* (2013.01)

(58) Field of Classification Search
CPC .............................. A61K 31/352; A61P 9/10
See application file for complete search history.

(56) References Cited

U.S. PATENT DOCUMENTS

| 8,673,368 B2 | 3/2014 | Guy et al. |
| 9,205,063 B2 | 12/2015 | Guy et al. |
| 2004/0034108 A1 | 2/2004 | Whittle |
| 2005/0070596 A1 | 3/2005 | Baker et al. |

(Continued)

FOREIGN PATENT DOCUMENTS

| GB | 2 376 464 A | 12/2002 |
| GB | 2 377 633 A | 1/2003 |

(Continued)

OTHER PUBLICATIONS

GB0601013.6, dated May 25, 2006, Search Report.
(Continued)

*Primary Examiner* — San Ming R Hui
(74) *Attorney, Agent, or Firm* — Wolf, Greenfield & Sacks, P.C.

(57) ABSTRACT

The present invention relates to cannabinoids for use in the prevention or treatment of neurodegenerative diseases or disorders. Preferably the cannabinoids are cannabichromene (CBC) cannabidivarin (CBDV) and/or cannabidivarin acid (CBDVA). More preferably the neurodegenerative disease or disorder to be prevented or treated is Alzheimer's disease.

10 Claims, 10 Drawing Sheets

(56) References Cited

U.S. PATENT DOCUMENTS

| | | |
|---|---|---|
| 2006/0039959 A1 | 2/2006 | Wessling |
| 2010/0239693 A1 | 9/2010 | Guy et al. |
| 2014/0377382 A1 | 12/2014 | Guy et al. |

FOREIGN PATENT DOCUMENTS

| | | | |
|---|---|---|---|
| GB | 2 391 865 A | | 2/2004 |
| GB | 2 392 093 A | | 2/2004 |
| GB | 2 434 312 A | | 7/2007 |
| GB | 2 450 493 A | | 12/2008 |
| GB | 2 479 153 A | | 10/2011 |
| WO | WO 02/32420 A1 | | 4/2002 |
| WO | WO 02/064109 A2 | | 8/2002 |
| WO | WO 02/069993 A1 | | 9/2002 |
| WO | WO 02/089945 A2 | | 11/2002 |
| WO | WO 03/037306 A2 | | 5/2003 |
| WO | WO 03/105800 A2 | | 12/2003 |
| WO | WO 2004/016246 A1 | | 2/2004 |
| WO | WO 2006/054057 A2 | | 5/2006 |
| WO | WO2007/083098 | * | 7/2007 |
| WO | WO 2008/024490 A2 | | 2/2008 |
| WO | WO 2013/005017 A1 | | 1/2013 |

OTHER PUBLICATIONS

GB0601013.6, dated Mar. 16, 2011, Examination Report.
GB1111261.2, dated Jun. 13, 2012, Search Report.
PCT/GB2007/000122, dated Jun. 5, 2007, International Search Report and Written Opinion.
PCT/GB2007/000122, dated Feb. 1, 2008, International Preliminary Report on Patentability.
PCT/GB2012/051540, dated Aug. 7, 2012, International Search Report and Written Opinion.
PCT/GB2012/051540, dated Jun. 20, 2013, Written Opinion.
PCT/GB2012/051540, dated Oct. 29, 2013, International Preliminary Report on Patentability.
[No Author Listed] Cannabinoid. Wikipedia. Version as edited on Jun. 28, 2007. http://en.wikipedia.org/wiki/Cannabinoid. 11 pages.
Ali Ibn-e-Abbaas Majoosi; Kaamil-al-Sena'ah, Part II (10th Century AD), Central Council for Research in Unani Medicine, 61-65 Institutional Area, Janak Puri, New Delhi-58, 2005AD, pp. 116.
Ayurveda Sarasamgrahah—Shri Baidyanath Ayurveda Bhavan Limited, Calcutta, Edn. 2003, pp. 467.
Berman et al., Efficacy of two cannabis based medicinal extracts for relief of central neuropathic pain from brachial plexus avulsion: results of a randomised controlled trial. Pain. Dec. 2004;112(3):299-306.
Carroll et al., Cannabis for dyskinesia in Parkinson disease. A randomized double-blind crossover-study, Neurology 2004; 63:1245-1250.
Di Marzo et al., Plant, synthetic, and endogenous cannabinoids in medicine. Annu Rev Med. 2006;57:553-74.
Esposito et al., Cannabidiol in vivo blunts beta-amyloid induced neuroinflammation by suppressing IL-1beta and iNOS expression. Br J Pharmacol. Aug. 2007;151(8):1272-9. Epub Jun. 25, 2007.
Hampson et al., Cannabidiol and (-)Delta9-tetrahydrocannabinol are neuroprotective antioxidants. Proc Natl Acad Sci U S A. Jul. 7, 1998;95(14):8268-73.
Hampson et al., Neuroprotective antioxidants from marijuana. Ann N Y Acad Sci. 2000;899:274-82.
Hayakawa et al., Therapeutic Potential of Non-Psychotropic Cannabidiol in Ischemic Stroke. Pharmaceuticals. 2010; 3(7):2197-2212.
Iuvone et al., Cannabidiol: a promising drug for neurodegenerative disorders? CNS Neurosci Ther. 2009 Winter;15(1):65-75. doi: 10.1111/j.1755-5949.2008.00065.x.
Izzo et al., Non-psychotropic plant cannabinoids: new therapeutic opportunities from an ancient herb. Trends Pharmacol Sci. Oct. 2009;30(10):515-27.
Kichuk et al., Regulation of nitric oxide production in human coronary microvessels and the contribution of local kinin formation. Circulation. Jul. 1, 1996;94(1):44-51.
Kuiper et al., Decreased cerebrospinal fluid nitrate levels in Parkinson's disease, Alzheimer's disease and multiple system atrophy patients. J Neurol Sci. Jan. 1994;121(1):46-9.
Maksimović et al., Effects of nerve and fibroblast growth factors on the production of nitric oxide in experimental model of Huntington's disease. Vojnosanit Pregl. Mar.-Apr. 2002;59(2):119-23.
Mohammad Azam Khan; Ikseer Azam, vol. I (19th century AD), Munshi Nawal Kishore, Lucknow, Fourth Edition, pp. 54.
Mohammad Azam Khan; Muheet-e-Azam vol. III (19 th century AD), Matba Nizami, Kanpur, 1887 AD, pp. 147.
Mohammad Najmul Ghani Khan; Khazaain-al-Advia, vol. I (20 th century AD), Nadeem Yunus Printer/Sheikh Mohd Basheer & Sons, Lahore, 1911 AD, pp. 886.
Mohammad Najmul Ghani Khan; Khazaain-al-Advia, vol. III (20th century AD), Nadeem Yunus Printer/Sheikh Mohd Basheer & Sons, Lahore, 1926 AD, pp. 77.
Rasatantrasarah Evam Siddhaprayogasamgrahah—part II; Krishan Gopal Ayurveda Bhawan; Edn 8th; 1990; pp. 288-289.
The United Kingdom Parliament, Select Committee on Science and Technology Ninth Report (1998) at http://www.parliament.the-stationery-office.co.uk/pa/ld199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.
Third Party Submission Under Art 37 CFR 1.99 "Patent publication No. 20100239693, filed Jun. 4, 2010 & published on Sep. 23, 2010 with U.S. Appl. No. 12/087,847".
Vaney et al., Efficacy, safety and tolerability of an orally administered cannabis extract in the treatment of spasticity in patients with multiple sclerosis: a randomized, double-blind, placebo controlled, crossover study, Multiple Sclerosis 2004; 10:417-424.
Wade et al., A preliminary controlled study to determine whether whole-plant cannabis extracts can improve intractable neurogenic symptoms, Clinical Rehabilitation 2003; 17:21-29.
Wade et al., Do cannabis-based medicinal extracts have general or specific effects on symptoms in multiple sclerosis? A double-blind, randomized, placebo-controlled study on 160 patients, Multiple Sclerosis 2004; 10:434-441.

* cited by examiner

FIG. 1  Each bar shows the mean ±_SEM of 5 experiments in triplicate.

***P <0.001 vs control; °°°P <0.001, °°P <0.01 and °P <0.05 vs Aß.

Each bar shows the mean ± SEM of 5 experiments in triplicate.

***P <0.001 vs control; °°°P <0.001, °°P <0.01 and °P <0.05 vs Aβ.

Each bar shows the mean ± SEM of 3 experiments.

***P <0.001 vs control; °°°P <0.001 vs Aβ.

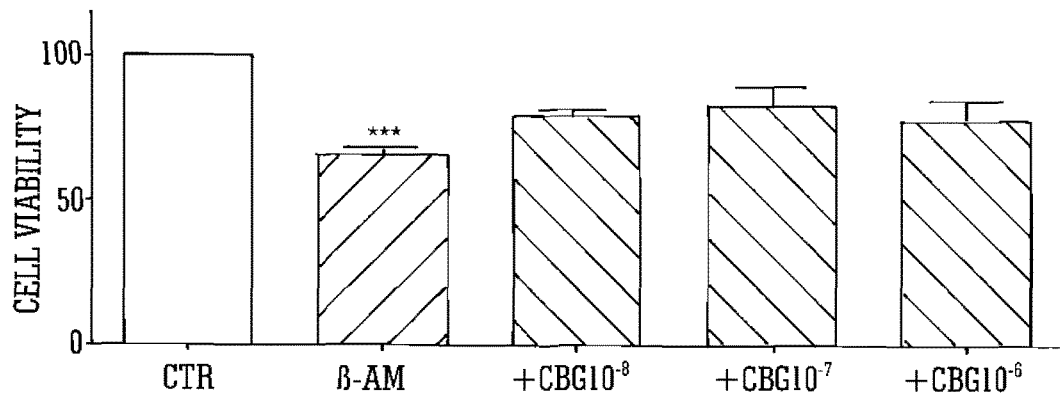
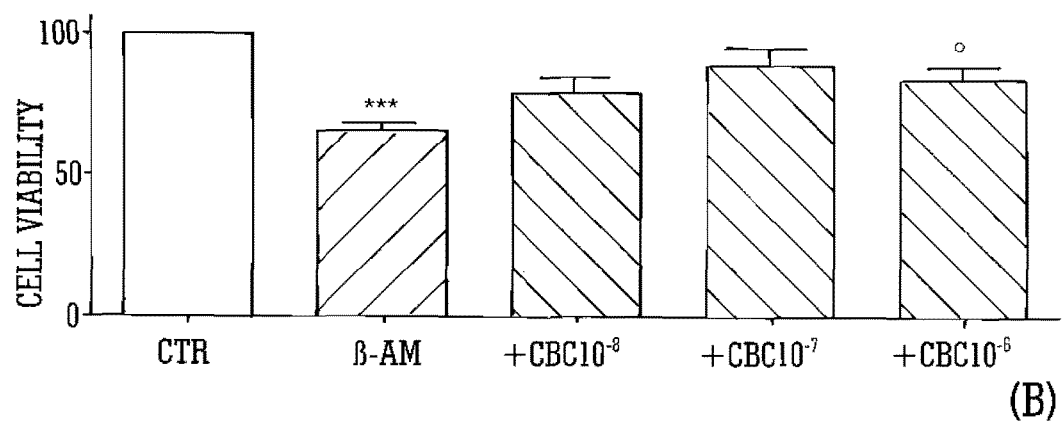
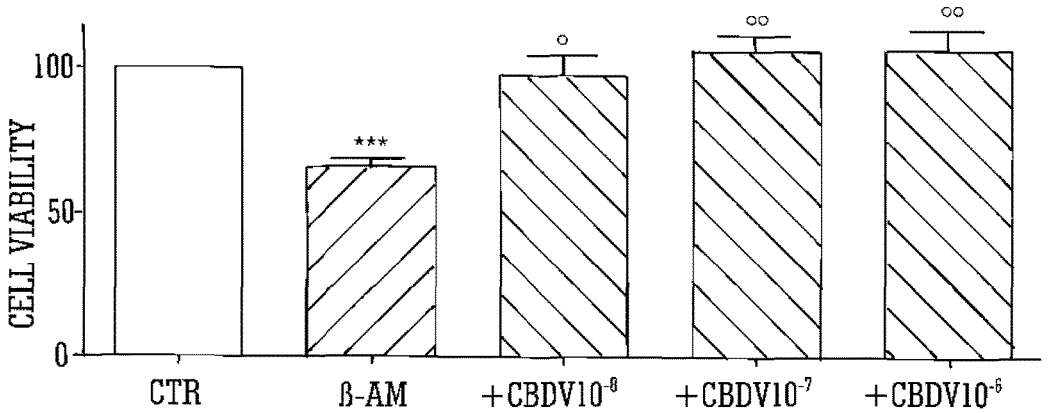
Each bar shows the mean ± SEM of 3 experiments.
***P <0.001 vs control; °°°P <0.001, °°P <0.01 and °P <0.05 vs Aβ.
FIG. 4

CANNABINOIDS FOR USE IN THE TREATMENT OF NEURODEGENERATIVE DISEASES OR DISORDERS

The present invention relates to cannabinoids for use in the prevention or treatment of neurodegenerative diseases or disorders. Preferably the cannabinoids are cannabichromene (CBC) cannabidivarin (CBDV) and/or cannabidivarin acid (CBDVA). More preferably the neurodegenerative disease or disorder to be prevented or treated is Alzheimer's disease.

BACKGROUND TO THE INVENTION

Neurodegenerative diseases or disorders are caused by the progressive damage or death of neurons. Neurons are nerve cells in the brain whose primary function is to assist in the memory process. The damage or death of neurons leads to a gradual deterioration of the functions controlled by the affected part of the nervous system.

Neurodegenerative diseases or disorders often occur as a result of oxidative stress. Oxidative stress occurs to the cells in an organism when the effects of pro-oxidants (such as free radicals, reactive oxygen and reactive nitrogen species) exceed the ability of anti-oxidants to neutralise them. When levels of free radicals or other pro-oxidants increase to such an extent, they can cause damage to cell membranes which in turn may result in cell death or damage to genetic material.

The group of neurodegenerative diseases or disorders are characterised by changes in the normal neuronal function, leading, in most cases, to neuronal death. Most of these diseases are associated, especially in late stages, with severe neuronal loss.

With an increasingly ageing population more and more people are affected by neurodegenerative diseases or disorders. According to the National Institute of Neurological Disorders and Stroke, there are more than 600 different neurodegenerative diseases or disorders.

Some of the most common types of neurodegenerative diseases or disorders include Alzheimer's disease, Parkinson's disease and Multiple sclerosis.

The process of degeneration of the neurons in an organism is often as a result of glutamate excitotoxicity. Glutamate is a signalling chemical and under normal conditions the concentration of glutamate tends to be quite low. Glutamate is required at these low concentrations for crucial brain functions such as memory and learning. When glutamate concentrations increase, the process of neurodegeneration begins.

When the brain is deprived of oxygen either due to a neurodegenerative disease, such as Alzheimer's disease, or a neurodegenerative disorder such as an ischemic event (such as a stroke), or due to trauma (such as a closed head injury), an abnormal build-up of glutamate occurs.

Neurodegeneration takes place when the glutamate attaches to receptor proteins on a cells surface. These N-methyl-D-aspartate (NMDA) receptors then open an excess of calcium channels causing the intracellular concentration of calcium to increase rapidly. Calcium ions activate phospholipase A (PLA), which in turn results in the release of arachidonic acid and superoxide radicals.

Neurodegeneration proceeds from the destructive effects of oxidative radicals caused by the glutamate flood. The radicals cause disruption of essential reactions in the neurones and this leads to degeneration or death of the cell.

Some neuroprotective agents have been studied in clinical trials in stroke patients. One drug Dextrorphan is of limited use however due to its side effects of hallucinations, agitation and hypotension.

Another drug, Selfotel, unfortunately showed trends towards a higher mortality rate with patients treated with the drug rather than placebo, and as such the trials were halted. The drug Cerestat also had its trials terminated because of concerns with the benefit-to-risk ratio of the drug.

Clearly there is a significant requirement for an efficacious treatment to prevent or treat neurodegenerative diseases or disorders.

Cannabinoids are a group of chemicals known to activate cannabinoid receptors in cells. Phytocannabinoids are the cannabinoids derived from cannabis plants. Endocannabinoids are endogenous cannabinoids found in humans and other animals. The phytocannabinoids can be isolated from plants or produced synthetically. When isolating the phytocannabinoids from plants they can be purified to the extent that all of the other naturally occurring compounds, such as, other minor cannabinoids and plant molecules such as terpenes are removed. This purification results in a purity of greater than 99% (w/w) of the target cannabinoid.

It was discovered that glutamate toxicity could be prevented to some extent by pure/synthetic preparations of the cannabinoids tetrahydrocannabinol (THC) or cannabidiol (CBD), (Hampson et al. 1998). The cannabinoids were tested in vitro on neuronal cultures exposed to glutamate. Although further research from an in vivo study by the same group failed to find a difference between animals treated with pure CBD and the placebo treated animals (Rosenthal et al. 2000).

The cannabinoid cannabidiol (CBD) is known to exhibit neuroprotective, anti-inflammatory and anti-oxidant properties and as such has been tested in models of neuro-toxicity and neurodegeneration. Promising results have been achieved with CBD in the control of toxicity induced by β-amyloid peptide, which is responsible for the neurodegeneration in Alzheimer's patients (Iuvone et al. 2009).

The beneficial effects of CBD in the treatment of neurodegenerative diseases in an in vivo model of Alzheimer's disease have also been demonstrated (Esposito et al. 2007).

The application GB2479153 demonstrates the anti-epileptic effects of the phytocannabinoid CBDV.

The application GB2450493 discusses the CB1 and CB2 cannabinoid receptor antagonist properties of the phytocannabinoid CBG.

The International application WO 2008/024490 discusses the potential for cannabinoid agonists to be used to treat opioid abuse.

The patent application GB2377633 discusses formulations which comprise THC and CBD and may also comprise CBDV.

In the granted United Kingdom patent, GB2432312, the applicants demonstrated that the administration of cannabinoids, as extracts from cannabis plants, were more efficacious than that of the purified compounds, in the prevention of neural degeneration. In particular cannabinoid-rich extracts comprising as a predominant cannabinoid either tetrahydrocannabinol (THC) or cannabidiol (CBD) were particularly efficacious in the prevention of neurodegeneration. The applicants additionally found that a combination of the two cannabinoid extracts were particularly effective neuroprotectants.

At least 85 different cannabinoids have been isolated from the cannabis plant and their structures differ depending on where cyclisation of the precursor cannabinoid cannabigerol (CBG) occurs. It is well known that the different cannabinoids demonstrate different properties. For example the cannabinoid tetrahydrocannabinol (THC) is a known agonist of the CB1 receptor; however the propyl variant of this cannabinoid, tetrahydrocannabivarin, (THCV), has been shown to act in an opposite manner at the CB1 receptor and is classed as a CB1 antagonist. It should therefore be appreciated that although the class of cannabinoids are all found to be produced in various strains of the cannabis plant it cannot be assumed that they all share the same properties.

The cannabinoid cannabidiol (CBD), unlike THC and THCV shows little activity at the CB1 or CB2 receptors.

In the present application, the applicants have discovered that further cannabinoids which are molecularly distinct from CBD, THC and THCV are able to prevent or treat neurodegenerative diseases or disorders. These cannabinoids are: cannabichromene (CBC), and cannabidivarin (CBDV). The model of neurodegenerative disease exemplified by the applicants is Alzheimer's disease.

Alzheimer's disease is the most prevalent neurodegenerative disease affecting elderly people. In 2006 there were 26.6 million sufferers of the disease worldwide and it is predicted that by 2050 Alzheimer's disease will affect 1 person in 85 globally. The cause and progression of the disease are not well understood and the currently used treatments only offer a small symptomatic benefit. There are currently no treatments which are able to delay or halt the progression of the disease. More than 500 clinical trials have been conducted for identification of a possible treatment for Alzheimer's disease yet there still remains a lack of suitable treatment options.

BRIEF SUMMARY OF THE DISCLOSURE

In accordance with a first aspect of the present invention there is provided one or more of the phytocannabinoids: cannabichromene (CBC) cannabidivarin (CBDV) and/or cannabidivarin acid (CBDVA), for use in the prevention or treatment of neurodegenerative diseases or disorders.

Preferably the one or more phytocannabinoids is CBDV.
Preferably the one or more phytocannabinoids is CBDVA.
Preferably the one or more phytocannabinoids is CBC.

The term "neurodegenerative disease or disorder" is used to describe different diseases or disorders which include but are not limited to: neurodegenerative diseases, ischemic diseases, brain injury or damage and age-related or autoimmune neural degeneration.

The term "prevention" is taken to mean preventing a disease or disorder from occurring, rather than curing or treating symptoms of said disease or disorder.

The term "treatment" is taken to mean curing a disease or disorder rather than treating symptoms of said disease or disorder.

In accordance with a second aspect of the present invention there is provided the use of one or more of the phytocannabinoids: cannabichromene (CBC) cannabidivarin (CBDV) and/or cannabidivarin acid (CBDVA), in the manufacture of a medicament for use in the prevention or treatment of neurodegenerative diseases or disorders.

In accordance with a third aspect of the present invention there is provided a method of preventing or treating neurodegenerative diseases or disorders which comprises administering to a subject in need thereof a therapeutically effective amount of one or more of the phytocannabinoids: cannabichromene (CBC), cannabidivarin (CBDV) and/or cannabidivarin acid (CBDVA).

Neurodegenerative diseases or disorders arise when degeneration of the neural pathway occurs as a result of a specific disease. Ischemic diseases arise when degeneration of the neural pathway occurs as a result of lack of oxygen. Brain injury or damage occurs when degeneration of the neural pathway occurs as a result of an injury to the brain itself. Age-related or autoimmune neural degeneration arise when degeneration of the neural pathway occurs as a result of the patient's age or due to an autoimmune disease.

Preferably the neurodegenerative disease or disorder is taken from the group: Alzheimer's disease; Parkinson's disease; amyotrophic lateral sclerosis; or Huntington's disease.

More preferably the neurodegenerative disease or disorder to be prevented or treated is Alzheimer's disease.

Alternatively the neurodegenerative disease or disorder is taken from the group: stroke; cardiac ischemia; coronary artery disease; thromboembolism; myocardial infarction or an ischemic related disease.

Preferably the one or more of the cannabinoids are present in a daily dose effective to prevent or treat neurodegenerative diseases or disorders. Preferably the effective daily dose of cannabinoid/s is between 5 mg and 1000 mg. More preferably the effective daily dose of cannabinoid/s is between 5 mg and 100 mg.

In a further embodiment of the present invention the one or more of phytocannabinoids are used in combination with one or more other medicinal substances.

Preferably the one or more cannabinoids are in the form of a botanical drug substance (BDS).

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 75% of the phytocannabinoid-containing fraction, more preferably still greater than 85% of the phytocannabinoid-containing fraction, and more preferably still greater than 95% of the phytocannabinoid-containing fraction.

In some cases, such as where the principle cannabinoid is CBDV the amount of the principle phytocannabinoid in the BDS is lower. Here the amount of phytocannabinoid is preferably greater than 55% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 10% (w/w) of the total extract, more preferably still less than 5% (w/w) of the total extract, and most preferably the minor phytocannabinoid is present in an amount less than 2% (w/w) of the total extract.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

In a further embodiment of the present invention there is provided a composition comprising one or more of the phytocannabinoids: cannabichromene (CBC) and/or cannabidivarin (CBDV), for use in the prevention or treatment of neurodegenerative diseases or disorders.

BRIEF DESCRIPTION OF THE DRAWINGS

Embodiments of the invention are further described hereinafter with reference to the accompanying drawings, in which:

FIG. 4 shows the effects of CBG, CBC and CBDV on Aβ-induced SH-SY5Y cell viability;

DETAILED DESCRIPTION

Figure 1:
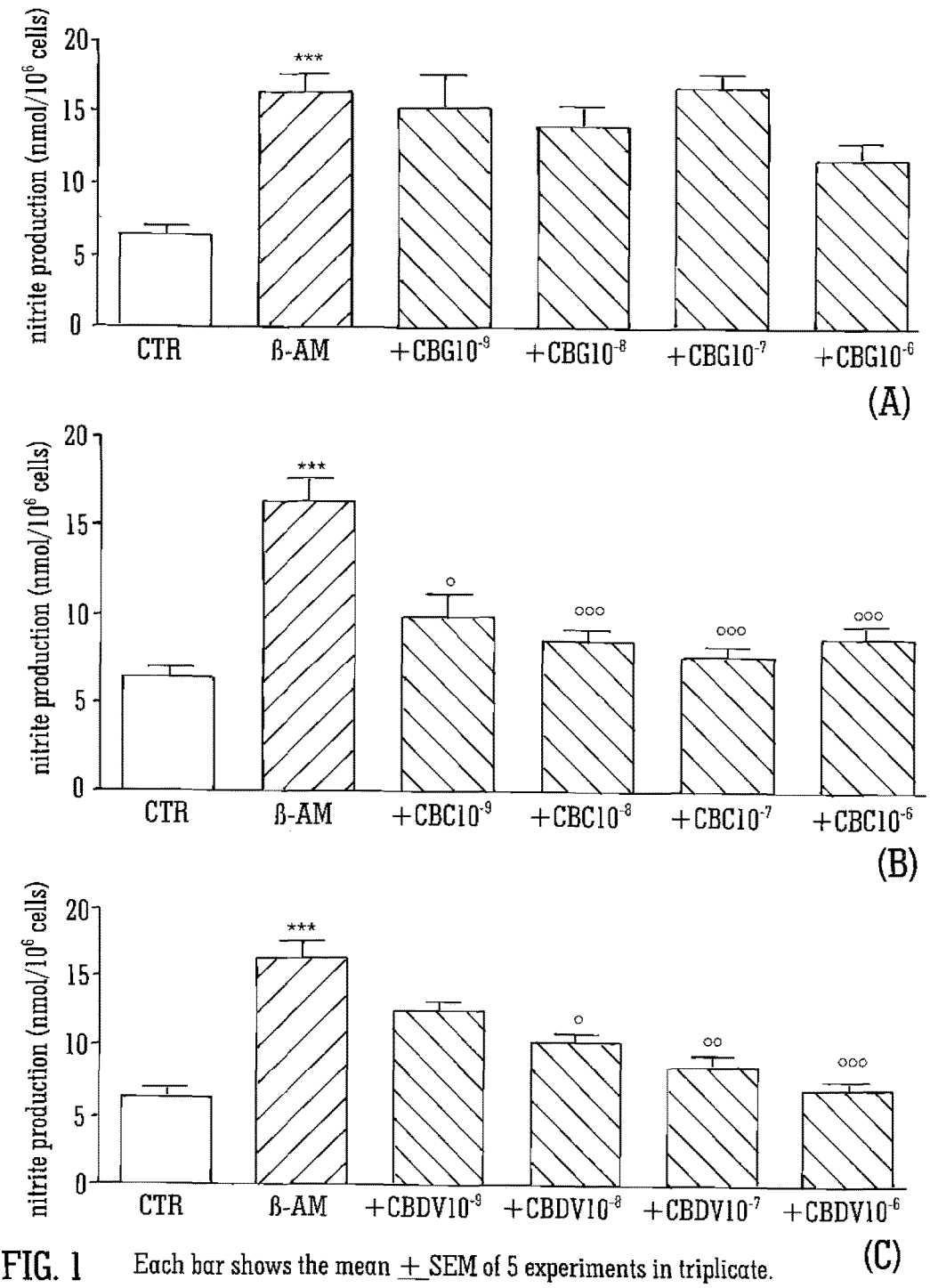
FIG. 1 shows the effect of CBG, CBC and CBDV on nitrite production in Aβ-stimulated C6 cells.

The Examples below demonstrate the results obtained using six different which have not previously been demonstrated as having the ability to prevent or treat neurodegenerative diseases or disorders.

In addition Example 2 also includes data for CBD, a known neuroprotectant, for comparison purposes.

Example 1: The Effects of Cannabinoids in a Model of Neurodegenerative Disease

Materials and Methods

The cannabinoids tested were CBG, CBC, and CBDV. The cannabinoids were isolated from cannabis plant material and purified. The cannabinoids were tested at a concentration of $10^{-9}$ to $10^{-6}$ M. The cannabinoids were dissolved in DMSO at the concentration of $10^{-2}$M and then diluted in DMEM to their final concentration.

Glial cells (C6) were cultured in 10% FBS supplemented DMEM. PC12 neuronal cell were cultured in 10% FBS plus 5% HS supplemented DMEM and SHY-5SY neuronal cells were cultured in 10% FBS supplemented RPMI. Neuronal cells were differentiated with retinoic acid. After 24 hours of starvation glial cells, differentiated PC12 and SHY-5SY neuronal cells were treated with the cannabinoids, CBC, CBG and CBDV, in the presence or absence of 1 µg/mL of Aβ (1-42) for the following 24 hours.

Cell viability was determined using 3(4,5-dimethylthiazol-2yl)2,5-diphenyl-2H-tetrazolium bromide (MTT) assay which is an assay based on the ability of viable cells to convert MTT in formazan salt.

The cells were plated in 96-well culture plates at the density of $5 \times 10^3$ cells/well and allowed to adhere at 37° C. for 2 hours. Thereafter, the medium was replaced with fresh medium and the cells were treated as above described. After 24 hours 25 µl MTT (5 mg/ml in DMEM) was added to the cells and incubated for additional 3 hours at 37° C. After this time, the cells were lysed and the dark blue crystals solubilized with 125 µl of a solution containing 50% (v/v) N,N, dimethylformamide, 20% (w/v) sodium dodecylsulphate, with an adjusted pH of 4.5. The optical density of each well was measured with a microplate spectrophotometer (Titertek Multiscan MCC/340) equipped with a 620 nm filter.

Production of NO was assayed by measuring the amount of nitrite in the culture medium of C6 cells 24 hours after Aβ(1-42) (1 µg/mL) stimulation using a spectrophotometric assay based on Griess reaction.

The mRNA level of iNOS in C6 cells was determined using the semi-quantitative RT-PCR method. The PCR-primers were selected according to appropriate DNA sequences. 15 µl aliquots of PCR products were electrophoretically fractionated through 1% agarose gel containing the fluorescent Vistra green dye. Labelling intensity of the PCR product, which is linear to the amount of DNA, was quantified using the Molecular Imager FX and Quantity One software (Biorad, Milan, Italy).

Results are expressed as mean±SEM of n experiments. Statistical analysis was performed using analysis of variance (ANOVA) and multiple comparisons were performed by Bonferroni's test with P<0.05 considered significant.

Results

FIG. 1 shows the effect of (A) CBG, (B) CBC and (C) CBDV on nitrite production in Aβ-stimulated C6 cells. The treatment of C6 cells with Aβ (1-42) (1 µg/mL) for 24 hours determined a significant increase in nitrite production, the stable metabolite of nitric oxide. The results indicate that both CBC and CBDV ($10^{-9}$ to $10^{-6}$M) treatment significantly reduced, in a concentration dependent manner, the nitrite production in Aβ-stimulated C6 cells. In contrast, CBG ($10^{-9}$ to $10^{-6}$M) had no effect on this parameter. Each bar shows the mean±SEM of 5 experiments in triplicate. ***P<0.001 vs control; °°°P<0.001, °°P<0.01 and °P<0.05 vs Aβ.

Figure 2:
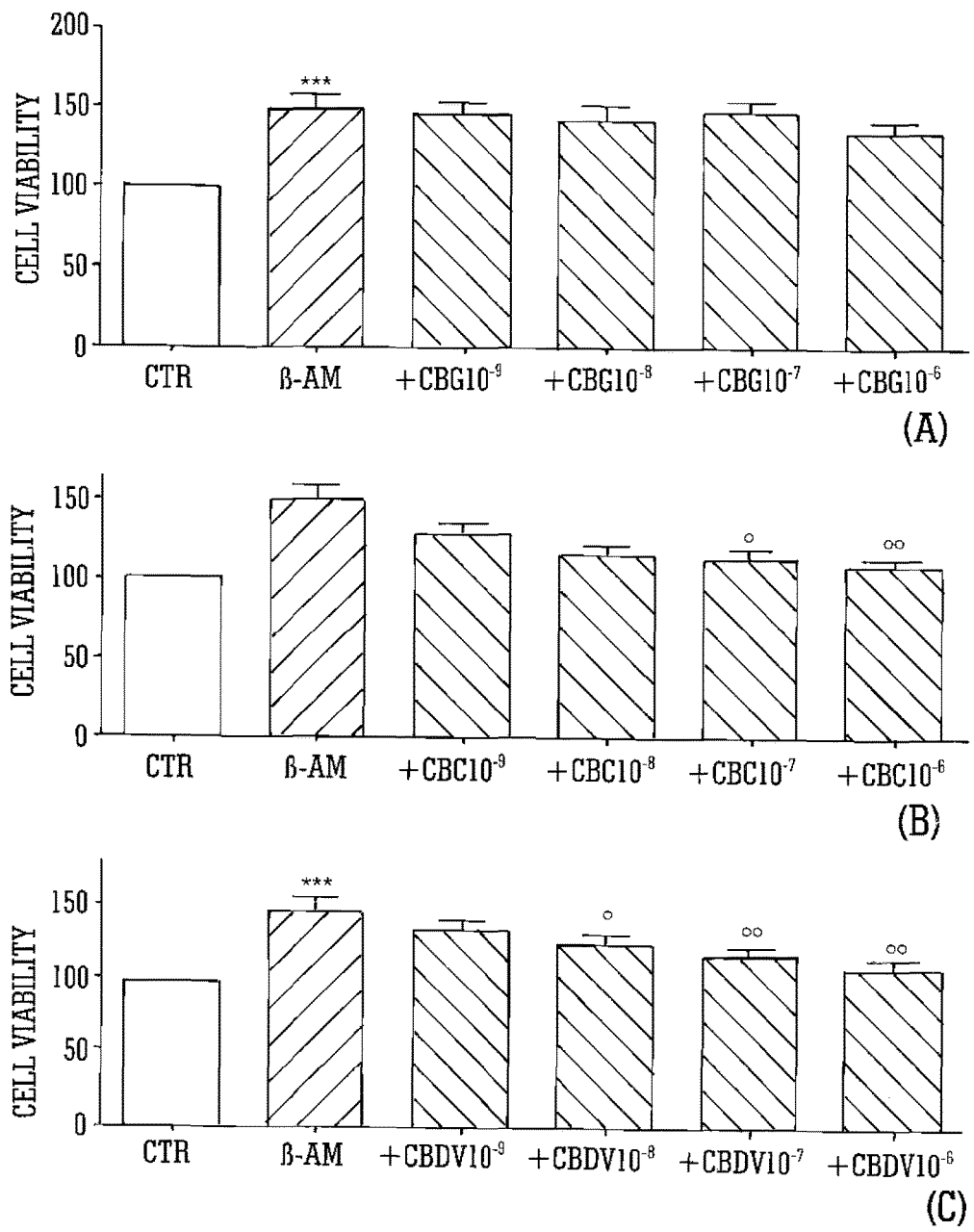
FIG. 2 shows the effect of CBG, CBC and CBDV on Aβ-stimulated C6 cell viability.

FIG. 2 shows the effect of (A) CBG, (B) CBC and (C) CBDV on Aβ-stimulated C6 cell viability. The treatment of C6 cells with Aβ (1-42) (1 µg/mL) for 24 hours determined a significant increase in cell viability measured as the ability of proliferating cells to convert MTT in formazan salt. The treatment with CBC ($10^{-7}$ to $10^{-6}$ M) and CBDV ($10^{-8}$ to $10^{-6}$ M), significantly inhibited cell proliferation in a concentration dependent manner. In contrast, CBG ($10^{-9}$ to $10^{-6}$ M) had no effect on the parameter under study. Each bar shows the mean±SEM of 5 experiments in triplicate. ***P<0.001 vs control; °°°P<0.001, °°P<0.01 and °P<0.05 vs Aβ.

Figure 3:
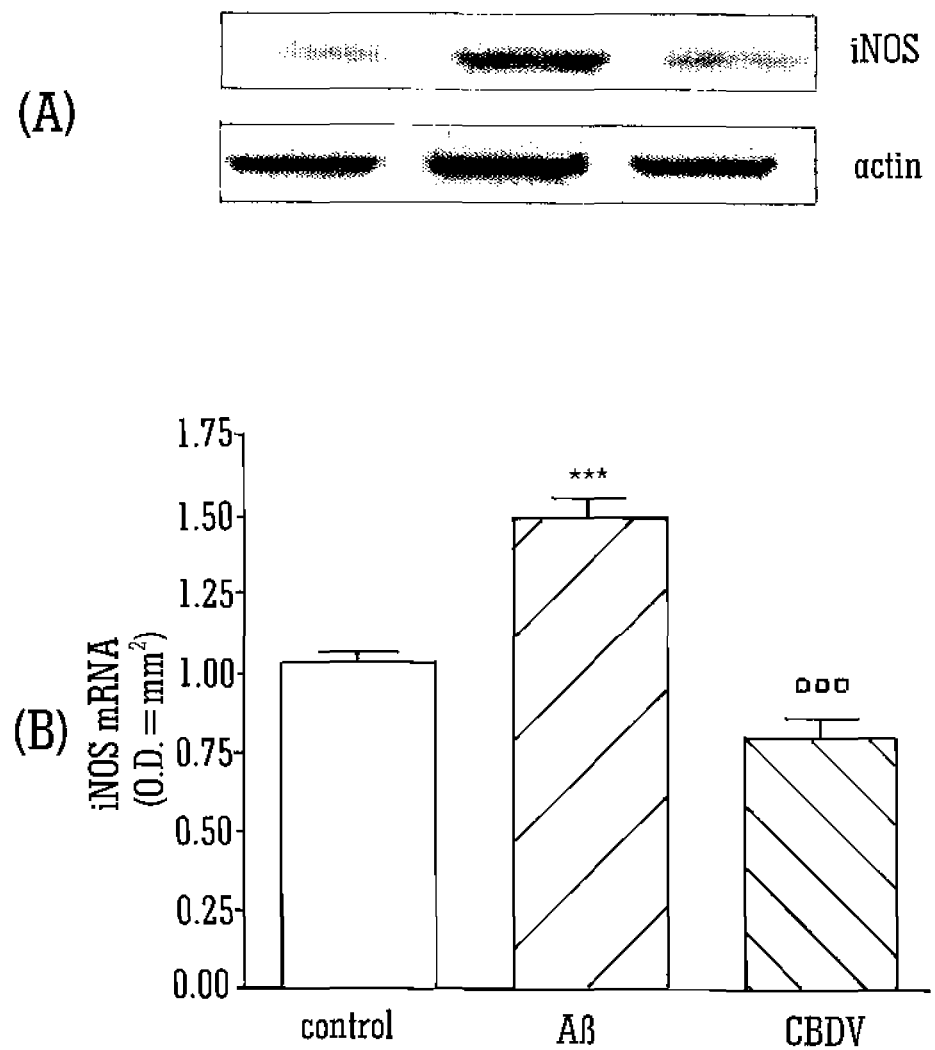
FIG. 3 shows the effects of CBDV on iNOS transcription in Aβ-stimulated C6 cells.

FIG. 3 shows the effect of CBDV on iNOS transcription in Aβ-stimulated C6 cells. The treatment of C6 cells with Aβ (1-42) (1 µg/mL) for 24 hours determined a significant increase in the levels of iNOS mRNA. The administration of CBDV ($10^{-7}$ M) resulted in significant reduction of mRNA transcription. Panel A shows iNOS mRNA in C6 cell homogenates; (B) densitometric analysis of corresponding bands (optical density). The panel is representative of n=3 separated experiments. Each bar shows the mean±SEM of 3 experiments. ***P<0.001 vs control; °°°P<0.001 vs Aβ.

FIG. 4 shows the effect of CBG, CBC and CBDV on Aβ-induced SH-SY5Y cell viability. The treatment of SH-SY5Y cells with Aβ (1-42) (1 µg/mL) determined a significant reduction in cell viability measured as the ability of viable cells to convert MTT in formazan salt. The results indicate that administration of CBDV ($10^{-9}$ to $10^{-6}$ M) was able to prevent, in a concentration dependent manner and significantly, Aβ-induced SHSY-5SY cell death; whereas CBC was effective only at the highest concentration used ($10^{-6}$ M). In contrast, CBG ($10^{-9}$ to $10^{-6}$M) had no effect on the parameter under study. Each bar shows the mean±SEM of 3 experiments. ***P<0.001 vs control; °°°P<0.001, °°P<0.01 and °P<0.05 vs Aβ.

Conclusion

The data presented in this example indicate that both CBDV and CBC, but not CBG, are able to significantly reduce the Aβ-dependent glial cell proliferation and activation; moreover CBDV and, at least in part, CBC are also able to decrease the neurotoxicity induced by Aβ treatment, in in vitro experiments.

This Example demonstrates the neuroprotective properties of two of the cannabinoids studied, namely CBC and CBDV. For example, the ability of these cannabinoids to decrease the amount of nitrite produced in the glial cells which had undergone treatment to simulate neurodegeneration means that these cannabinoids are effective neuroprotectants. Reduction in the level of nitrite produced is a key parameter in the study of many neurological diseases and disorders including Alzheimer's disease, Parkinson's disease, amyotrophic lateral sclerosis, Huntington's disease, stroke or heart disease (Kuiper et al., 1994), (Makisimovic et al. 2002), and (Kichuk et al. 1994).

Similarly the ability of CBC and CBDV to prevent neuronal cell death provides credible evidence that these cannabinoids act as neuroprotectants in a model of neurodegeneration. It is clear that an increase in glial cell viability is vitally important in the prevention or treatment of diseases and disorders including Alzheimer's disease, Parkinson's disease, amyotrophic lateral sclerosis, Huntington's disease, stroke or heart disease.

Example 2: The Neuroprotective Effects of Cannabidivarin (CBDV)

Materials and Methods

Glial cells (C6) were cultured in 10% FBS supplemented DMEM, and SHY-5SY were cultured in 10% FBS supplemented RPMI. Neuronal cells were differentiated with retinoic acid. After 24 hours of starvation glial cells and SHY-5SY were treated with CBDV ($10^{-7}$M), CBD ($10^{-7}$ M), CBDVA ($10^{-7}$ M), CBDA ($10^{-7}$ M) and THCVA ($10^{-7}$ M) in presence or absence of Aβ (1-42) (1 µg/mL) for following 24 hours. All tested compounds were dissolved in DMSO at the concentration of $10^{-2}$ M and then diluted in DMEM; DMSO at final dilution that did not show any effects on the parameters under study.

Cell activation/viability was determined using 3(4,5-dimethylthiazol-2yl)2,5-diphenyl-2H-tetrazolium bromide (MTT) assay, an assay based on the ability of viable cells to convert MTT in formazan salt. Briefly, the cells were plated in 96-well culture plates at the density of $5 \times 10^3$ cells/well and allowed to adhere at 37° C. for 2 hours. Thereafter, the medium was replaced with fresh medium and the cells were treated as above described. After 24 hours 25 µl MTT (5 mg/ml in DMEM) was added to the cells and incubated for additional 3 hours at 37° C. After this time, the cells were lysed and the dark blue crystals solubilized with 125 µl of a solution containing 50% (v/v) N,N, dimethylformamide, 20% (w/v) sodium dodecylsulphate, with an adjusted pH of 4.5. The optical density of each well was measured with a microplate spectrophotometer (Titertek Multiscan MCC/ 340) equipped with a 620 nm filter.

In another set of experiments cell counting was performed by TC10 System (BIO-RAD), according to manufacturing instruction.

Western blot analysis was performed on C6 and SHY-5SY cell lysate. Briefly cells were rapidly homogenized in 60 µl of ice-cold hypotonic lysis buffer [10 mM HEPES, 1.5 mM $MgCl_2$, 10 mM KCl, 0.5 mM phenylmethylsulfonyl fluoride, 1.5 µg/mL soybean trypsin inhibitor, pepstatin A 7 µg/mL, leupeptin 5 µg/mL, 0.1 mM benzamidine, 0.5 mM dithiothreitol (DTT)]. After this time, the cytoplasmic fractions were then obtained by centrifugation at 13000 g for 10 min and protein concentration in the samples was determined with Bio-Rad assay kit according to the manufacturer's instructions. Immunoblotting analysis of iNOS, COX-2, TNF-a, Bcl2 and actin were performed on a cytosolic fraction. Protein concentration was determined and equivalent amounts (50 µg) of each sample were separated under reducing conditions in 12% SDS-polyacrylamide minigel. The proteins were transferred onto nitrocellulose membrane according to the manufacturer's instructions (Bio-Rad Laboratories, Hercules, Calif., USA). Depending upon the experiments, the membranes were blocked by incubation at 4° C. overnight in high salt buffer (50 mM Trizma base, 500 mM NaCl, 0.05% Tween-20) containing 5% bovine serum albumin; they were then incubated for 1 h with anti-iNOS (1:1000 v/v) (Oncogene, San Diego, Calif.), anti-COX-2 (1:500 v/v) (Cayman Chemical, UK), anti-TNF-a (Sigma Aldrich), anti-Bcl2 (Santa Cruz laboratories,) and anti-actin (1:1000) (Santa Cruz laboratories,) for 2 h at room temperature, followed by incubation with specific horseradish peroxidase (HRP)-conjugate secondary antibody (Dako, Golstrup, DK). The immune complexes were developed using enhanced chemiluminescence detection reagents (Amersham, Italy), according to the manufacturer's instructions and developed by Image-Quant Apparatus (GE Healthcare). The protein bands were scanned and densitometrically analyzed with a GS-800 imaging densitometer (Bio-Rad Laboratories, Calif., USA).

ELISA assay was performed on supernatants of cultured cells. Nunc Maxisorp 96-well microtiter plates (Gibco, Paisley, UK) were coated overnight at 4° C. with 1 µg/well of specific monoclonal antibody anti-TNF, diluted in 0.5 M $Na_2CO_3$. The wells were washed three times and then blocked with phosphate-buffered saline (PBS) containing 0.05% (v/v) Tween 20 and 0.3% Fetal Bovine Serum (ELISA buffer) for 30 min at room temperature. The standards and samples were added in a 100-µl volume and incubated at 37° C. for 1.5 h. The standard curve was generated using 0.1 ng to 1 µg/well of purified protein, diluted in ELISA buffer. Following four washes in ELISA buffer, monoclonal antibodies were diluted and added to the wells for 1 h. The wells were washed four more times and then incubated with the secondary antibody: anti-mouse Ig, biotinylated species-specific F(ab8)2 fragment from donkey (Amersham), diluted 1:1000 for 1 h. Following a further four washes the wells were incubated with 100 µl of streptavidinbiotinylated horseradish peroxidase complex (Amersham) diluted 1:1000 in ELISA buffer for 1 h. After a final six washes in ELISA buffer, 200 µl of a 0.4 mg/mL solution of o-phenylenediamine dihydrochloride (OPD, Sigma) in a 0.05 M phosphate citrate buffer was added to each well and colour was allowed to develop for up to 10 min. The colour reaction was stopped by addition of HCl and optical densities at 490 nm were measured using a microplate reader.

Results are expressed as mean±SEM of n experiments. Statistical analysis was performed using analysis of variance (ANOVA) and multiple comparisons were performed by Bonferroni's test with P<0.05 considered significant.

Results

Figure 5:
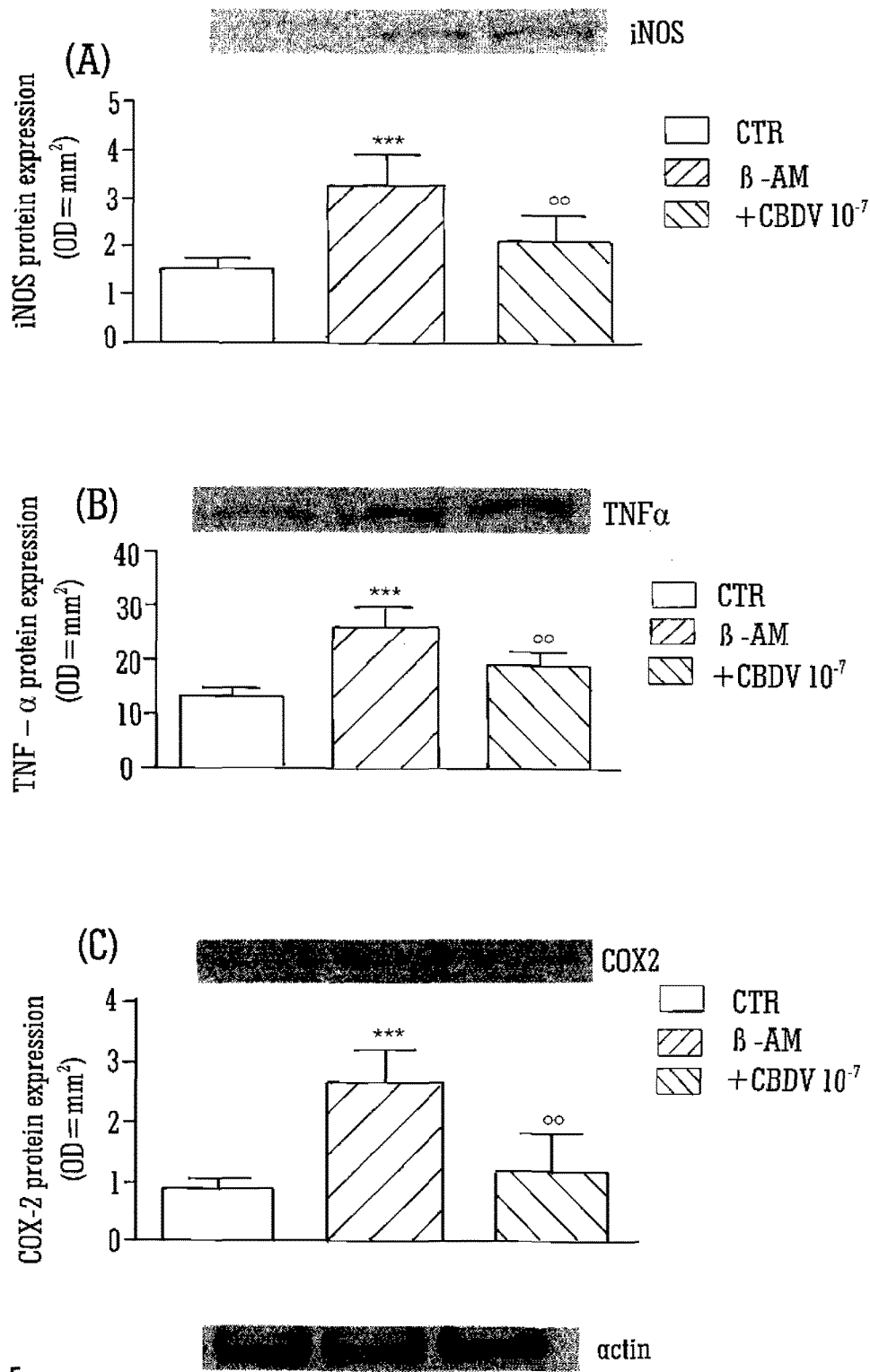
FIG. 5 shows the effect of CBDV on iNOS, TNF-α and COX2 expression in Aβ-stimulated C6 cells.

FIG. 5 demonstrates that C6 cells were treated with Aβ (1-42) (1 µg/mL) for 24 hours in the presence or absence of CBDV ($10^{-7}$ M) and protein expression was evaluated by western blot analysis. The treatment of C6 cells with Aβ 1 µg/mL) determined a significant increase in TNF-alpha (A), COX2 (B) and iNOS (C) protein expression. The administration of CBDV ($10^{-7}$ M) to Aβ-stimulated cells resulted in a significant reduction of TNF-alpha (A), COX2 (B) and iNOS protein expression. The figure shows the densitometric analysis of western blot bands (optical density); the panel is representative of n=3 separated experiments. Each bar shows the mean±SEM of 3 experiments. ***P<0.001 vs control; °°P<0.01., °°°P<0.001 vs Aβ.

Figure 6:
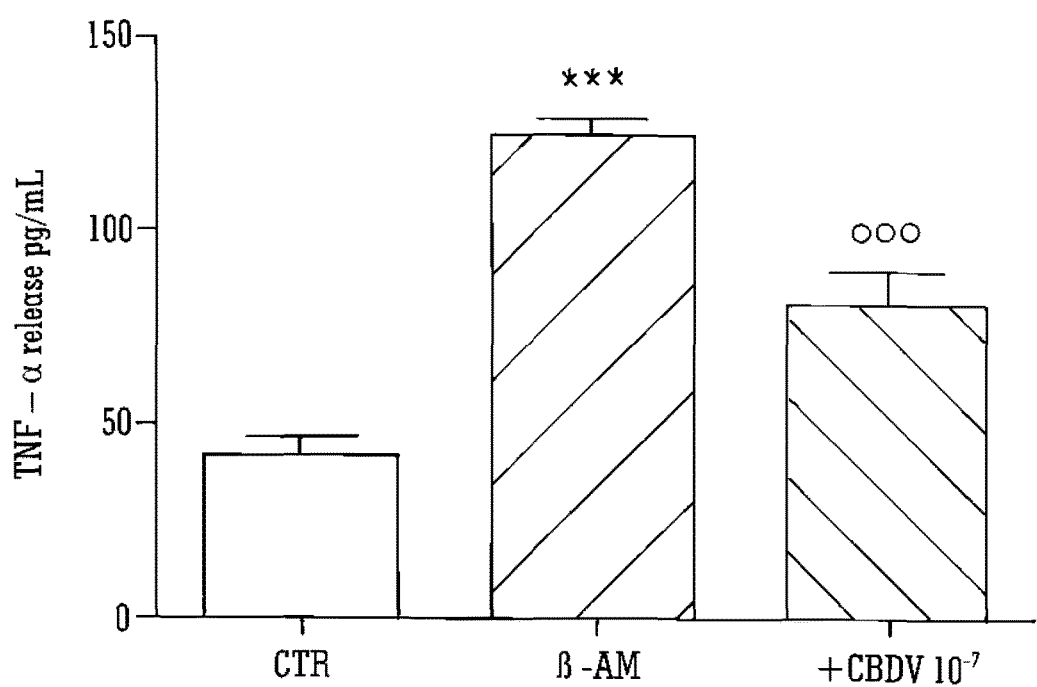
FIG. 6 shows the effect of CBDV on Aβ-induced TNF-α release.

FIG. 6 demonstrates the C6 cells that were treated with Aβ (1-42) (1 µg/mL) for 24 hours in the presence or absence of CBDV ($10^{-7}$ M) and TNF-alpha release in cell supernatant was evaluated by ELISA assay. The treatment with Aβ (1-42) (1 µg/mL) strongly increased the release of TNF-alpha When CBVD ($10^{-7}$ M) was administrated to Aβ treated C6 cells significantly reduced TNF-alpha release in the supernatant of cells. The panel is representative of n=3 separated experiments. Each bar shows the mean±SEM of 3 experiments. ***P<0.001 vs control; °°°P<0.001 vs Aβ.

Figure 7:
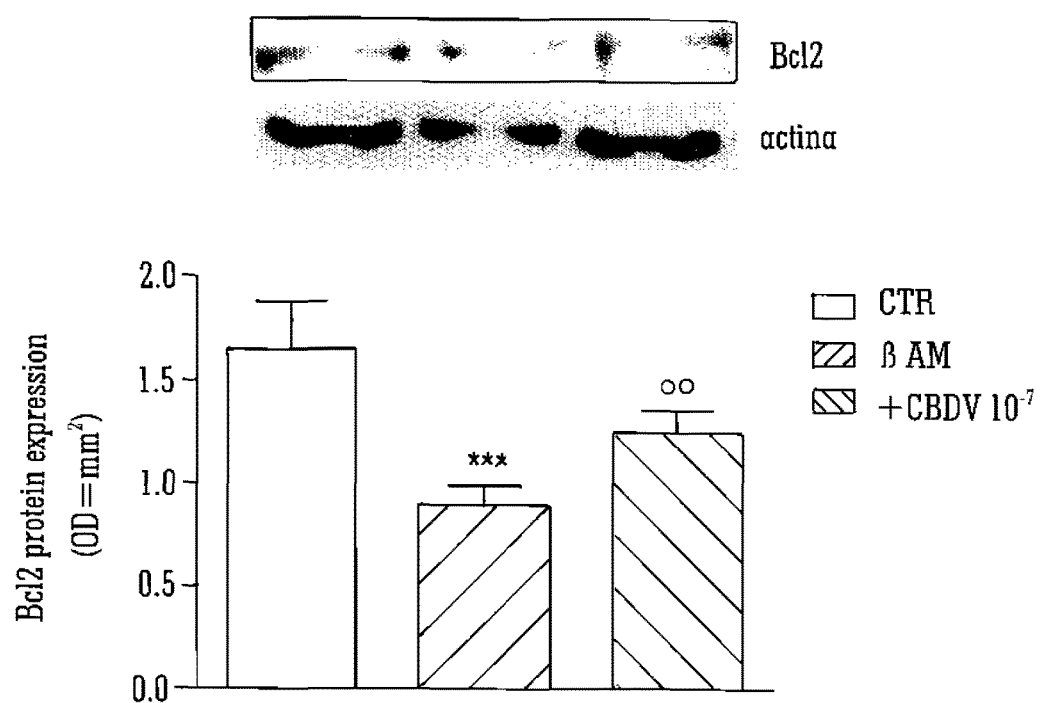
FIG. 7 shows the effect of CBDV on Aβ-induced BCl2 expression in SH-SY5Y cell.

FIG. 7 demonstrates the SH-SY5Y cells were treated with Aβ (1-42) (1 µg/mL) for 24 hours in the presence or absence of CBDV ($10^{-7}$ M) and protein expression was evaluated by western blot analysis. The treatment of SH-SY5Y cells with Aβ (1 µg/mL) determined a significant decrease in the expression of the anti-apoptotic protein Bcl2. The administration of CBDV ($10^{-7}$ M) to Aβ-stimulated cells significantly restored Bcl2 protein expression. The figure shows the densitometric analysis of western blot bands (optical density); the panel is representative of n=3 separated experiments. Each bar shows the mean±SEM of 3 experiments. ***P<0.001 vs control; °°P<0.01 vs Aβ.

Figure 8:
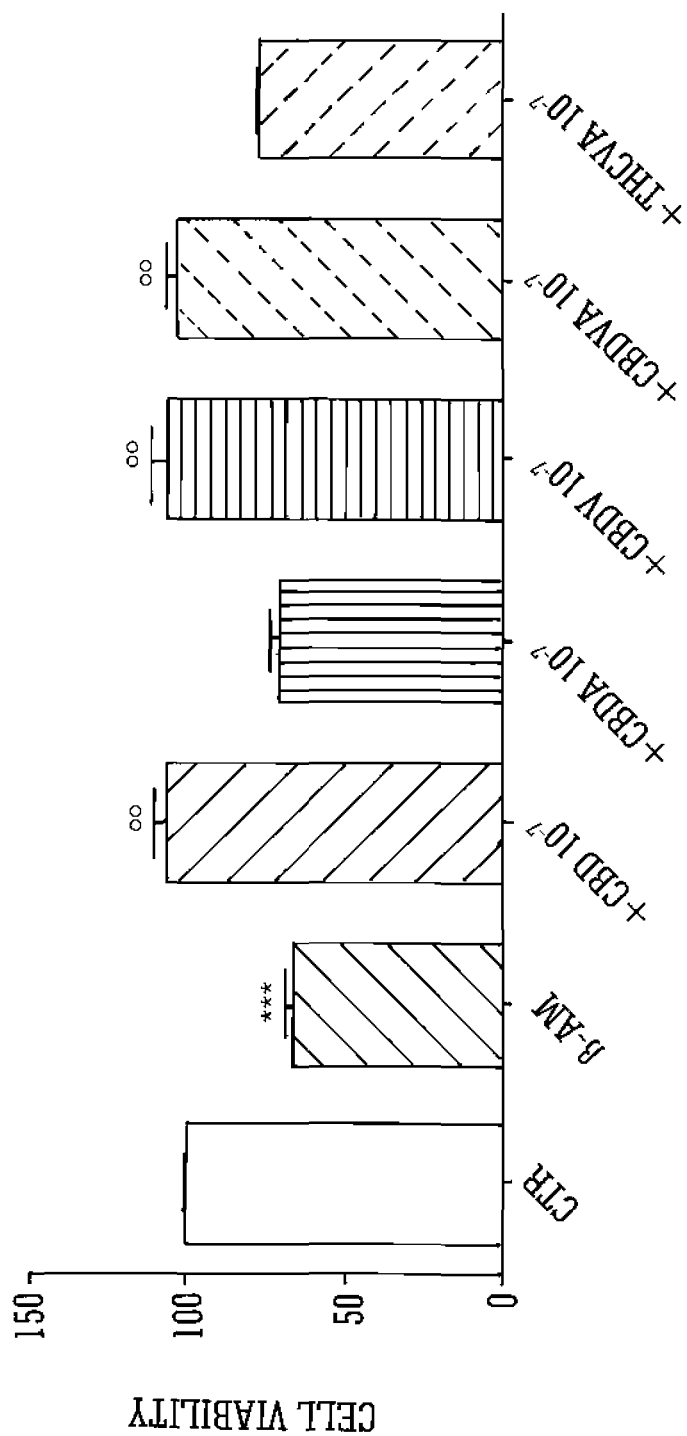
FIG. 8 shows the effect of CBD, CBDV, CBDA, CBDVA and THCVA on Aβ-induced SH-SY5Y activity.

FIG. 8 demonstrates the SH-SY5Y cells that were treated with Aβ (1-42) (1 µg/mL) for 24 hours in the presence or absence of CBD ($10^{-7}$ M), CBDV ($10^{-7}$ M), CBDA ($10^{-7}$ M), CBDVA ($10^{-7}$M) and THCVA ($10^{-7}$M) and cell viability was evaluated by MTT/formazan test.

The treatment of SH-SY5Y cells with Aβ (1 µg/mL) determined a significant reduction of SH-SY5Y viability evaluated as the ability of viable cells to convert MTT in formazan salt. The administration of CBD, CBDV and CBDVA ($10^{-7}$ M) was able to prevent Aβ SHSY-5SY cell death; whereas CBDA and THCVA had no effect on the parameter under study. Each bar shows the mean±SEM of 3 experiments. ***P<0.001 vs control; °°P<0.01. vs Aβ.

Figure 9:
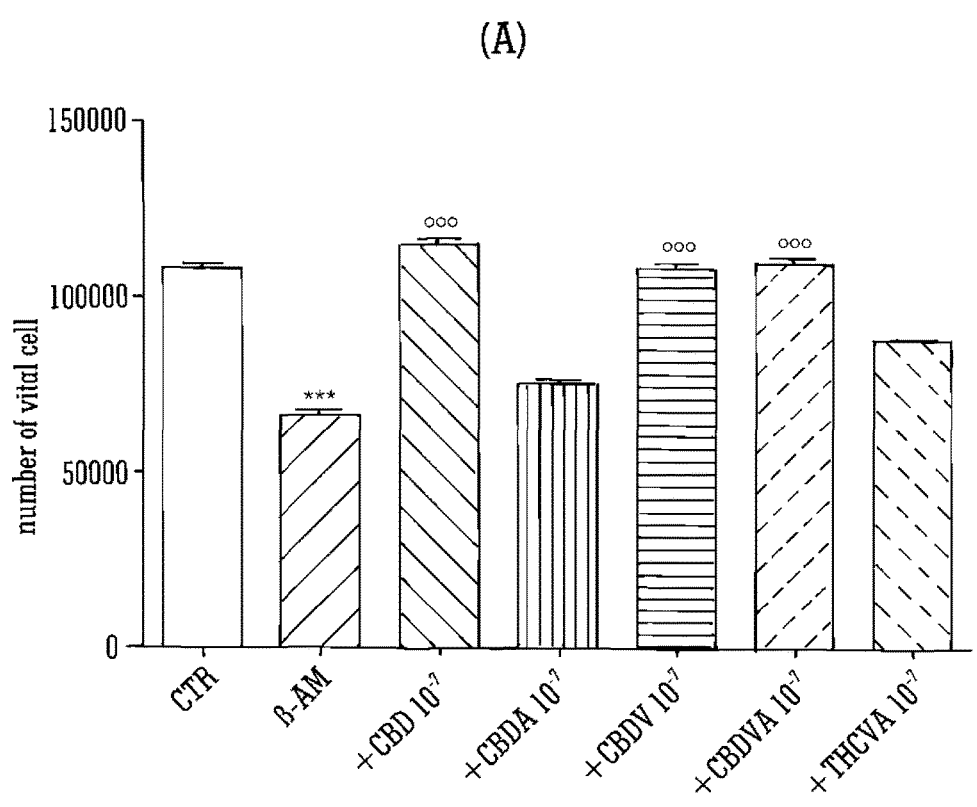
FIG. 9 shows the effect of CBD, CBDV, CBDA, CBDVA and THCVA on Aβ-induced SH-SY5Y viable cell number.
Figure 9:
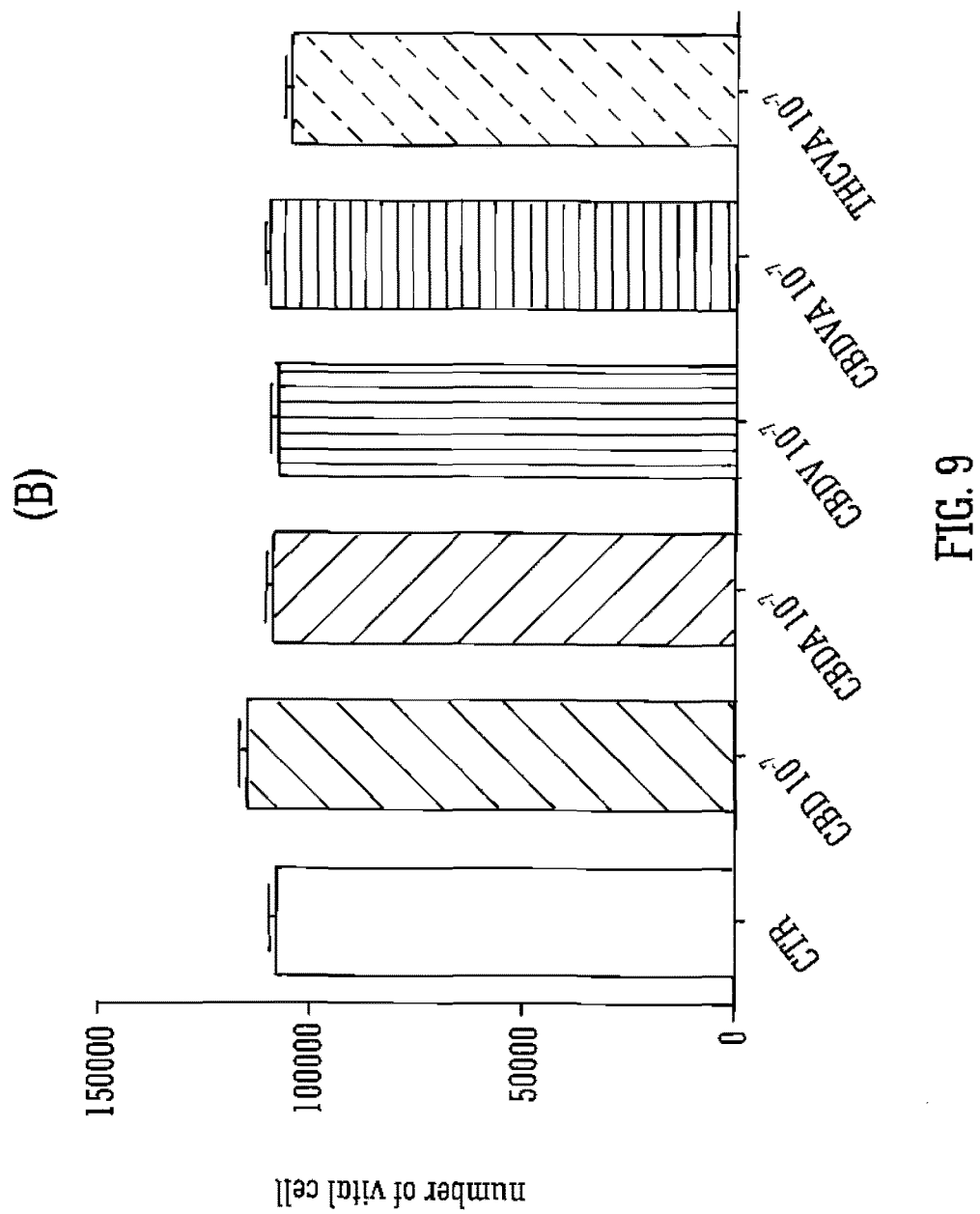

FIG. 9 details the treatment of SH-SY5Y cells with Aβ (1-42) (1 µg/mL) for 24 hours in the presence or absence of CBD ($10^{-7}$ M), CBDV ($10^{-7}$ M), CBDA ($10^{-7}$ M), CBDVA ($10^{-7}$ M) and THCVA ($10^{-7}$ M) and cell counting was performed by TC10 System (BIO-RAD), according to manufacturing instruction.

(A) The treatment of human neuronal cell-line, SH-SY5Y cells, with Aβ (1 µg/mL) determined a significant reduction in the viable cells. The effect of CBD, CBDV, CBDA. CBDVA and THCVA in preventing neuronal death was measured. The administration of CBD, CBDV, and CBDVA were able to prevent Aβ induced SHSY-5SY cell death. No significant effect was seen with CBDA and THCVA. (B) The tested compounds did not show any toxic effects at the tested concentration. ***P<0.001 vs control; °°P<0.005, vs Aβ.

Conclusions:

The data presented in this Example confirms the anti-inflammatory effect of CBDV in Aβ-activated glial cells and studies the possible anti-apoptotic role of CBDV.

Evidence that CBDV not only reduces the transcription of the pro-inflammatory proteins iNOS, COX-2 and TNF-alpha induced after Aβ insult to C6 cells but that it was also able to reduce the expression of these mediators.

Moreover, CBDV treatment results in a significant reduction of TNF-alpha release from Aβ-stimulated glial cells. In line with the evidence of a reduction in NO production by CBDV the here reported decrease of TNF-alpha production and release strongly support the anti-inflammatory action of CBDV during reactive gliosis.

Finally, these data indicate that CBDV is able to control the pro-inflammatory scenario triggered by Aβ acting at transcriptional level, i.e. by controlling the transcription of these important pro-inflammatory genes, and that this effects is accompanied also to the reduced expression and release of the corresponding protein products. These data suggest the involvement of transcriptional factors as NFkB, AP-1 etc in CBDV-mediated anti-inflammatory effects.

These data strongly support the protective effects of CBDV and CBDVA in Aβ toxicity both in astroglial and neuronal cells, suggesting therefore their usefulness in the treatment of Alzheimer's disease and other related diseases.

REFERENCES

Kichuk, M; Seyedi N; Zhang X; Marboe C; Michler R; Addonizio L; Kaley G; Nasjletti A; Hintze T., *Regulation of Nitric Oxide Production in Human Coronary Microvessels and the Contribution of Local Kinin Formation.* Circulation. 1994; 90:I-295

Kuiper M A; Visser J J; Bergmans P L; Scheltens P; and Wolters E C., *Decreased cerebrospinal fluid nitrate levels in Parkinson's disease, Alzheimer's disease and multiple system atrophy patients.* J Neurol Sci. 1994 January; 121(1):46-9.

Maksimoyić I D; Joyanoyić M D; Maliceyić Z; Colić M; and Ninković M., *Effects of nerve and fibroblast growth factors on the production of nitric oxide in experimental model of Huntington's disease.* Vojnosanit Pregl. 2002 March-April; 59(2):119-23.

The invention claimed is:

1. A method for treating neurodegenerative diseases or disorders comprising administering to a subject in need thereof a therapeutically effective amount of cannabinoids cannabidivarin (CBDV) and/or cannabidivarin acid (CBDVA), wherein the CBDV and/or CBDVA are isolated or purified.

2. The method of claim 1, wherein the cannabinoid is CBDV.

3. The method of claim 1, wherein the cannabinoid is CBDVA.

4. The method of claim 1, wherein the neurodegenerative disease or disorder is selected from the group consisting of: Alzheimer's disease; Parkinson's disease; amyotrophic lateral sclerosis; and Huntington's disease.

5. The method of claim 4, wherein the neurodegenerative disease or disorder to be prevented or treated is Alzheimer's disease.

6. The method of claim 1, wherein the cannabinoid/s are administered in a daily dose effective to prevent or treat neurodegenerative diseases or disorders.

7. The method of claim 6, wherein the effective daily dose of cannabinoid/s is between 5 mg and 1000 mg.

8. The method of claim 7, wherein the effective daily dose of cannabinoid/s is between 10 mg and 50 mg.

9. The method of claim 1, further comprising administering the cannabinoid/s in combination with one or more other medicinal substances.

10. The method of claim 1, wherein the cannabinoid/s are in the form of a botanical drug substance (BDS).

* * * * *